United States Patent
Allsup et al.

(10) Patent No.: US 9,110,854 B1
(45) Date of Patent: Aug. 18, 2015

(54) WEB-BASED COMMUNITY FOR DISABLED INDIVIDUALS

(75) Inventors: James F. Allsup, Scottsdale, AZ (US); Kelly M. Wisness-Semchee, Arnold, MO (US); Patrick T. Condon, St. Louis, MO (US); Mary Dale Walters, Belleville, IL (US)

(73) Assignee: Allsup, Inc., Belleville, IL (US)

( * ) Notice: Subject to any disclaimer, the term of this patent is extended or adjusted under 35 U.S.C. 154(b) by 699 days.

(21) Appl. No.: 13/154,646

(22) Filed: Jun. 7, 2011

Related U.S. Application Data (60) Provisional application No. 61/357,663, filed on Jun. 23, 2010.

(51) Int. Cl.
*G06F 15/16* (2006.01)

(52) U.S. Cl.
CPC ........................................ *G06F 15/16* (2013.01)

(58) Field of Classification Search
CPC .......................... H04L 29/08072; H04L 29/06
USPC ........................................................ 709/217
See application file for complete search history.

(56) References Cited

U.S. PATENT DOCUMENTS

| | | |
|---|---|---|
| 7,249,040 B1 | 7/2007 | Binns et al. |
| 7,328,183 B1 | 2/2008 | Leisle |
| 7,421,403 B2 | 9/2008 | Jacoby, Jr. |
| 2002/0143680 A1 | 10/2002 | Walters et al. |
| 2005/0278196 A1 | 12/2005 | Potarazu et al. |
| 2005/0283464 A1* | 12/2005 | Allsup et al. ..................... 707/3 |
| 2007/0072156 A1* | 3/2007 | Kaufman et al. ............. 434/236 |
| 2007/0233515 A1 | 10/2007 | Mehus et al. |
| 2009/0222290 A1 | 9/2009 | Crowe |
| 2010/0211403 A1 | 8/2010 | Allsup et al. |

* cited by examiner

*Primary Examiner* — Shripal Khajuria
(74) *Attorney, Agent, or Firm* — Polster, Lieder, Woodruff & Lucchesi, L.C.

(57) ABSTRACT

An Internet® or world wide web-based system that provides visitors access to databases that offer information and resources for support in coping with a mental or physical disability or an associated or similar condition. The visitor can access the status of a claim for Social Security Disability Insurance benefits, a personalized report on Medicare options or a personalized report on available financial resources and life plan products for persons with a disability. A Service Provider employs a computer and software technology to establish and maintain a website that allows the visitor to access, join, and participate in a virtual community of individuals having shared experiences and needs.

17 Claims, 4 Drawing Sheets

WEB-BASED COMMUNITY FOR DISABLED INDIVIDUALS

CROSS-REFERENCE TO RELATED APPLICATIONS

This application claims the benefit of provisional patent application Ser. No. 61/357,663, filed Jun. 23, 2010, which is incorporated herein by reference.

STATEMENT REGARDING FEDERALLY SPONSORED RESEARCH OR DEVELOPMENT

Not Applicable.

BACKGROUND OF THE INVENTION

The present invention relates generally to an Internet® or world wide web-based tool that offers visitors to a website personalized information and interactive resources to aid the individual in coping with the unique circumstances arising from a mental or physical disability and associated conditions.

Certain organizations or companies, at times referred to hereinafter as Service Providers, represent individuals with disabilities before the U.S. Social Security Administration (SSA) for purposes of obtaining Social Security Disability Insurance benefits (SSDI) for the disabled individual. The Service Provider also may provide services to the disabled individual who qualifies for Medicare. For example, a Service Provider may aid disabled individuals in the selection of a proper Medicare program, such as occurs in the assignee's Allsup Medicare Advisor® program, which meets specific needs or criteria of the individual.

Disabled individuals may require additional or supplemental services that extend beyond securing SSDI or providing Medicare options. Often a physical or mental disability is life changing for the individual. Job loss resulting from a disability, for example, can result in profound changes in the individual's mental or emotional condition, not to mention his or her financial status. The disabled individual, family members, caregivers or friends may need assistance in adapting to, or coping with, the physical, mental and lifestyle changes that accompany a disability. Although a Service Provider may provide a number of support services and resources for the disabled individual, the Service Provider is limited in the amount of time it can dedicate to any one individual. It would be advantageous if the disabled individual could obtain personalized information, access relevant resources, or find support services at a single source, anytime the individual chooses by computer through a web-based portal.

Moreover, it would be advantageous if the disabled individual could access, by computer through a single web-based portal, personalized information, such as health information, SSDI claim status, Medicare plan recommendations, health resources, news of interest to disabled individuals, message boards and interactive forums hosting topics of interest to persons with physical or mental disabilities.

SUMMARY OF THE INVENTION

The present invention comprises an Internet® or world wide web-based tool that offers visitors to the website support in coping with the unique circumstances arising from a mental or physical disability or associated or similar condition. The invention provides for a Service Provider that employs a computer and software technology to establish and maintain a website that allows the disabled individual, his or her family members, friends or caregivers to access by a computer a plurality of databases comprising relevant data and information as well as join and participate in a virtual community of individuals having shared experiences and needs. The visitor can participate in a supportive and caring environment that is available online anytime for the visitor's convenience.

In one aspect of the invention the portal allows access to the visitor's SSDI claims information whereby the visitor can monitor the progress of his or her claim for SSDI.

In another aspect of the invention the portal allows access to a Medicare Advisor Service (MAS) whereby the visitor can provide personal information for evaluation and obtain recommendations for acceptable Medicare plans based upon the visitor's information.

In yet another aspect of the invention, the portal allows access to a Disability Life Planning Service (DLPS), which is a system for providing an array of optimized services to a disabled individual which may include, but are not limited to, obtaining SSDI benefits from the SSA, management of lump sum payments of retroactive SSDI benefits, obtaining information on additional benefit programs, comprehensive lifestyle and financial planning for individuals with disabilities, MAS, tax planning, healthcare discount services, healthcare information, healthcare products and financial management through the use of stored value cards and accounts.

Another aspect of the invention comprises a website portal that allows the visitor to access specific web pages or databases of interest to the visitor. The visitor can access news, interactive forums, organizations, government agencies, medical information, blogs and other resources such as products and services of interest to individuals with disabilities, family members or caregivers.

BRIEF DESCRIPTION OF THE DRAWINGS

Corresponding reference numerals will be used throughout the several figures of the drawings.

DETAILED DESCRIPTION

The following detailed description illustrates the invention by way of example and not by way of limitation. This description will clearly enable one skilled in the art to make and use the invention, and describes several embodiments, adaptations, variations, alternatives and uses of the invention, including what we presently believe is the best mode of carrying out the invention. Additionally, it is to be understood that the invention is not limited in its application to the details of the arrangement and operation of components set forth in the following description or illustrated in the drawings. The invention is capable of other embodiments and of being practiced or being carried out in various ways. Also, it is to be understood that the phraseology and terminology used herein is for the purpose of description and should not be regarded as limiting.

In general, a web-based system, sometimes referred to as a community, hosted by a company or organization, referred to hereinafter as a Service Provider, is described. By way of example, the assignee of the instant patent application, Allsup, Inc., Belleville, Ill., is such a Service Provider. Therefore, for simplicity and clarity, the name "Allsup" may be employed at various times hereinafter or in the figures to denote one representative example of a Service Provider.

Generally speaking, the disclosure provides for a Service Provider that employs computer and software technology to establish and maintain a website that allows computer access to and use of various aspects of the invention. The Service Provider maintains a plurality of databases that include, but are not limited to, visitor data, resources, news sources, organizations, SSDI information, Medicare information and so forth.

For purposes of simplicity and clarity, users of, or a visitor to, the web-based community of the present invention may be referred to hereinafter as a "Visitor". In most cases the Visitor will be a disabled individual. However, the Visitor may be a family member, friend, caregiver, agent or attorney, or other individual in privity with, or having responsibility for, the disabled individual. Moreover, the Visitor may be a customer of one or more of the Service Provider's proprietary services and may be referred to as a Visitor/customer. Or the Visitor can be any member of the general public having an interest in the Service Provider's services and products. Hence the Visitor may not be a disabled individual, but may access the system on behalf of, or in the interest of, a disabled individual.

In general, the Visitor is permitted or allowed to access the web-based community via personal computer located at the Visitor's home, work place or any other site, usually remote from, the location of the Service Provider. However, the computer could be provided by the Service Provider, for example, through terminals, work stations or kiosks in the Service Provider's facility. The Visitor will access a web based community with the virtual aspects of any community including places of interest, a marketplace of services and products, and other Visitors.

Figure 1:
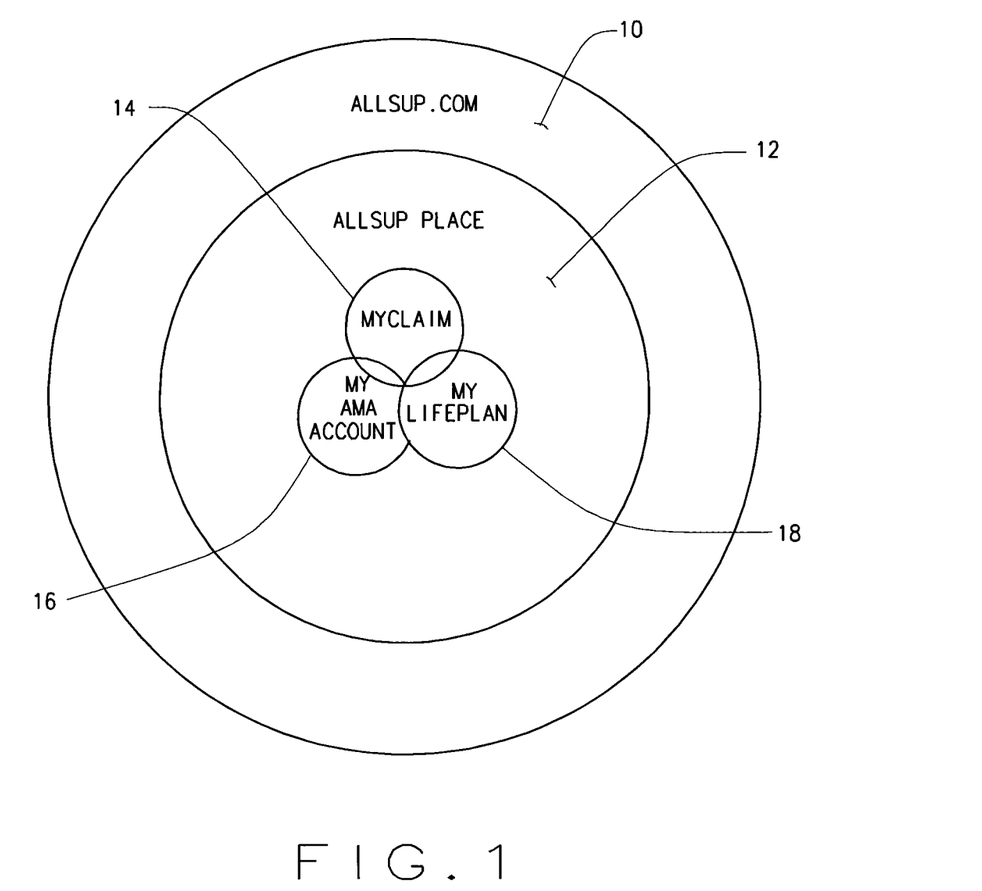
FIG. 1 is a circle diagram illustrating the integration of three components of the present invention.

Referring to FIG. 1, in one aspect of the invention the Service Provider maintains a website, indicated generally by reference numeral 10. The website may be accessed by a Visitor through the typical procedure of entering, on a general purpose computer connected to the Internet®, an appropriate domain name, represented in the illustrated example as Allsup.com. The Service Provider website 10 can be hosted on an appropriately programmed computer or server or the like maintained by the Service Provider or a third party host.

Another aspect of the present invention provides for a primary Internet® portal, indicated by reference number 12, through which a Visitor can enter the web-based community. By way of example, one embodiment of the portal hosted by the Service Provider is referred to as Allsup Place®. However, it will be appreciated that the name of the portal is incidental to the invention and any appropriate name for a site that allows the performance of the described and claimed functions is within the scope of the invention. It will be understood, particularly in view of FIG. 1, that portal 12 can be accessed through the Service Provider's website 10. Or, the portal to the web-based community can be accessed through a dedicated webpage or website or any other site, menu or link that performs the appropriate function. Entry of portal 12 effectuates entry into the web-based community including most aspects of the web-based community. Access can be provided in the form of a link actuated simply by clicking on the portal name appearing on a screen, for example "Allsup Place", or from a separate web page, a drop down menu, a tool bar or any other means provided by the web site, by the appropriate computer software or by the operating system.

Referring to FIG. 1 it will be appreciated that once the Visitor enters portal 12, he or she can then access different aspects of the invention. For example, in the illustrated embodiment, portal 12 provides access to at least three (3) major components of the invention. These components can be referred to as components, areas, sites, web pages or even neighborhoods of the virtual community. Although three major components of the community are shown, it will be understood that fewer than three or more than three are intended to be within the scope of the present invention.

As will be explained in greater detail below, certain aspects of the invention are available to all Visitors to website 10 who enter the on-line community through portal 12. However, not all of the major components are available to every Visitor who enters the portal. Access to various components of the invention may be limited or restricted to certain Visitors.

Referring specifically to the FIG. 1, portal 12, as illustrated, allows access to three proprietary services offered to Visitors by the Service Provider. In general, the three illustrated services require the Visitor to be a customer or client of the Service Provider. For example, the Visitor can access information regarding his or her claim for SSDI if he or she has retained the Service Provider to file a claim for SSDI. The Visitor can access the claim information through a link to a personalized record of the Visitor's SSDI claim. The link and the personalized record are referred to as MyClaim, indicated generally by reference number 14. Similarly, if the Visitor has enrolled in a proprietary Medicare Advisor Service (MAS), he or she can access personalized information regarding his or her Medicare coverage through a link, referred to in the illustration as MyAMA Account 16.

The Visitor also can access an extensive array of proprietary subservices and information of interest to a disabled individual through, for example, a link to a proprietary, personalized Disability Life Planning Service® (DLPS), through a portal referred to in the figure as MyLifePlan 18. In general, DLPS comprises an array of optimized services to a disabled individual including, but not limited to, obtaining SSDI benefits from the SSA, financial planning and management, tax planning, Medicare Advisor Service and healthcare discount services.

It will be noted from FIG. 1 that the three separate components, MyClaim, MyAMA Account and MyLifePlan overlap, indicating that once the Visitor enters the portal 12 he or she can visit any of the three services without having to login or take any other particular steps other than clicking on a link. Logging into portal 12 allows access to, and egress from, these sites. MyAMA Account, MyClaim and MyLifePlan, as well as other aspects of the instant invention, will be described in greater detail hereinafter. MAS and DLPS are described in greater detail in application Ser. No. 12/074,120, filed Feb. 11, 2010, which is incorporated herein by reference.

In general, the present invention provides a Visitor, particularly a disabled individual, with a personalized experience through the Internet®. The present invention provides, but is not limited to, many specific features personalized for each Visitor, depending upon the Visitor's status or level of activity.

Levels of Activity

Figure 2:
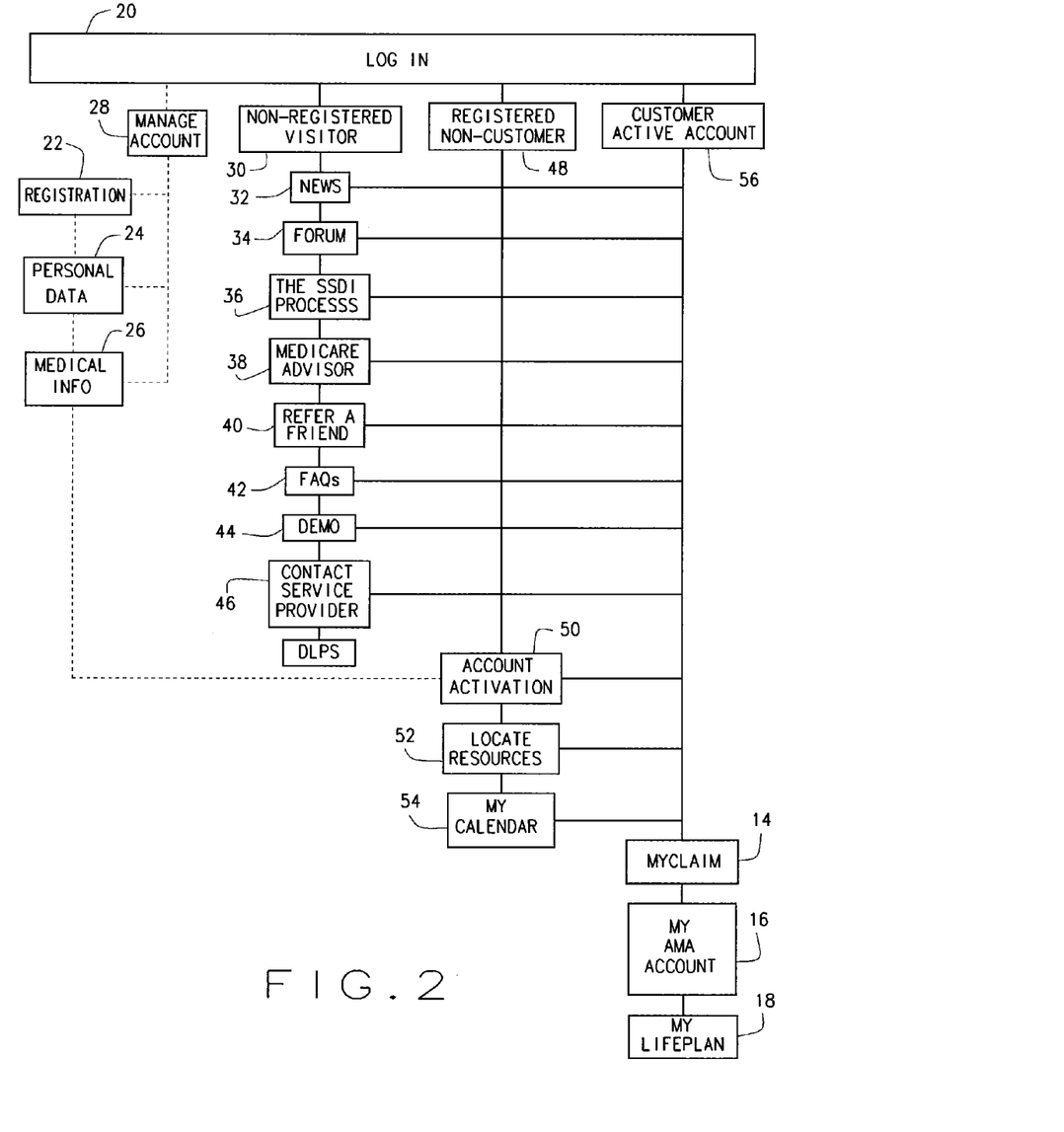
FIG. 2 is a block diagram illustrating the benefits and resources available to three different levels of visitors.

The invention provides three levels of activity within the web-based community depending upon whether the Visitor is a non-registered Visitor, a registered member of the web-based community, and/or a customer of the Service Provider with an activated customer account. The three levels of activity and features available to the respective Visitors are as follows:

A Non-Registered Visitor:
  News
  Forum
  The SSDI Process
  Medicare Advisor Service (MAS)
  Disability Life Planning Service (DLPS)
  Refer a Friend
  Allsup Place FAQs
  Allsup Place Demo-
    A printout of the Allsup Place Demo screens are attached hereto as Appendix A, and incorporated herein by reference.
  Contact Service Provider
A Registered Web-Based Community Member e.g Allsup Place Member (Non-Customer):
  Account Activation
  Locate Resources
  News
  Forum
  The SSDI Process
  Medicare Advisor Service (MAS)
  Disability Life Planning Service (DLPS)
  MyCalendar
  Refer a Friend
  Allsup Place FAQs
  Allsup Place Demo- See Appendix A
  Contact Allsup
A Service Provider Customer (with an Activated Customer Account):
  Account Activation
  MyClaim (available to SSDI customers only)
    Check the Status of a SSDI Claim
    My Contact Information
    Important Documents
    Contact Us
    Provide Us With Updates
  MyAMA Account (available to Allsup Medicare Advisor® (AMA) customers only)
    Check the Status of the AMA Report
    My Contact Information
    Access An AMA Report (including how to read the report)
    Contact Us
    Provide Us With Updates
  Medicare Advisor Service (MAS)
  Disability Life Planning Service (DLPS)
  MyLifePlan (available to Disability Life Planning Service® (DLPS) customers only)
    Check the status of the DLPS Report
    My Contact Information
    Access the DLPS Report
    Contact Us
    Access the DLPS Library (free additional resources)
  Locate Resources
  News
  Forum
  The SSDI Process
  MyCalendar
  Refer a Friend
  Allsup Place FAQs
  Allsup Place Demo- See Appendix A
  Contact Service Provider FIG. 2 illustrates in greater detail the levels of activity within the community available to Visitors and the relationship between the various levels and databases. Initially a Visitor can Log In 20 to the site. It will be noted that log in is required to access all levels of activity. The Visitor can become a registered Visitor by going through the registration process 22. Registration allows the Visitor to take advantage of more aspects of the web-based community. By registering, the Visitor sets up a personal account, selects a user name, display name, for use in the Forum, and a password.

The Visitor also enters basic information or Personal Data 24 such as name, address, phone number and email address. Other details may include, but are not limited to, information regarding specific medical conditions as Medical Information 26. The medical conditions most often are those the Visitor is suffering from (but not necessarily). Representative examples include, but are not limited to, AIDS/HIV, ALS, anxiety, arthritis, asthma, bipolar disorder, bulging discs, cancer, chronic fatigue syndrome, chronic pain, COPD, depression, diabetes, epilepsy, fibromyalgia, heart disease, hepatitis C, liver disease, Meniere's syndrome, MS, muscular dystrophy, organ transplants, Parkinson's disease, PTSD, spinal disorders, stroke and so forth. By entering medical conditions the Visitor allows aspects of the present invention to personalize resources, information, and news available to the Visitor.

The Visitor can make changes to the information provided through registration, such as the Visitor's profile, or change a password through the Manage Account 28 feature.

Even if the Visitor has not registered, he or she may still access useful information as a Non-registered Visitor 30. The Non-registered Visitor can access News 32 of interest to disabled individuals or their caregivers. In one representative embodiment, the News comprises a custom news feed which includes thousands of articles from a variety of news sources. The News feature is searchable. Each news article is a live link. News includes articles related to the Service Provider, disabilities in general, Social Security and Medicare issues.

The Visitor also can access a Visitor's Forum 34. The Visitor can post comments and read comments by others. The Service Provider facilitates the Forum by adding discussion topics. The Visitor may create a user profile, which is the information other Visitors can view.

Each Visitor can access information about the SSDI Process 36 via a link. The Visitor is provided information on the SSDI process, from information on each level, awarded rates, average days at that level to information on getting awarded and the Continuing Disability Review process. The Visitor can receive a step-by-step explanation of what happens during each level of the SSDI process. This information may also be obtained as a PDF document which can be printed out and used as a reference.

The Visitor also can access information concerning the Service Provider's Medicare Advisor Service (MAS) 38. If the Visitor is not a Service Provider Customer, as described in detail below, the Visitor still can access information regarding the Service Provider's MAS and a link to a free screening to determine if the Visitor is eligible for the MAS.

The Visitor also can Refer a Friend 40 to the web-based community by submitting the friend's email address, who then will receive a short email from the Visitor with a link to join the web-based community. The Visitor can access frequently asked questions concerning the web-based community, for example Allsup Place FAQs 42. The Visitor can actually view a demonstration of the web-based community and the features available to registered Visitors, for example at Allsup Place Demo 44. Finally, the Visitor can contact the Service Provider 46 to receive additional information regarding the community or other of the Service Provider's services. The Visitor is provided a Service Provider phone number and a web-based Contact form that allows the Visitor to submit a question or request.

The Log In 20 also provides access to the web-based community by a Registered Noncustomer 48. A Registered Noncustomer is a registered Visitor to the web-based community, but is not a customer or client of the Service Provider and does not receive certain proprietary services, such as SSDI representation, MAS or DLPS. It will be appreciated from FIG. 2 that the Registered noncustomer has access to all the information sites available to the Non-registered Visitor. However, some of the features are enhanced. For example, the Registered noncustomer Visitor can obtain additional News 32 features such as articles about various medical conditions (based on the medical conditions noted during the registration process), in addition to the articles available on the Service Provider, disabilities in general, Social Security and Medicare issues that are available to the Non-registered Visitor.

Furthermore, the Registered noncustomer has the ability to activate a personalized account through the Account Activation 50 if the Visitor becomes a customer of one or more of the Service Provider's proprietary services. As described above, the Registered noncustomer can provide personal data, list relevant Medical Information 26 or diseases to receive information on those conditions and allow customization of aspects of the invention based upon the Visitor's listed conditions or diseases and his or her state of residence. Account Activation 50 allows the Visitor to broaden the scope of his or her involvement in the community and manage the account as needed. As illustrated, there can be a relationship or sharing of information from databases associated with Registration 22, Personal Data 24, Medical Info. 26, Manage Account 28 and Account Activation 50.

The Registered noncustomer can access the Locate Resources 52 link. The Locate Resources section is pre-populated with information that can be personalized to the Visitor based upon information provided during Registration 22 and maintained in an appropriate database. For example, resources and products available to the Visitor may be based upon or targeted to, the Medical Information provided during registration. The Locate Resources section will identify relevant organizations, locate web resources and even provide personal stories about similarly situated individuals from the appropriate databases. Resources such as organizations can be condition-specific so as to be relevant to a Visitor having a specific physical or mental condition. Other resources may include a listing of benefit programs including free benefits that the Visitor may qualify for.

Moreover, the list of resources is customized to the Visitor's state of residency (noted during registration) so that the Visitor is apprised of resources within his or her locale. Hence, the organizations, for example, are provided by geographic area and accessible through a map screen and may be grouped together as condition-specific groups. The personal stories generally are of interest to, and applicable to, Visitors having a certain medical condition. A story can be accessed by clicking on a story title.

The web resources are maintained in appropriate databases and categorized by type of resource and can be accessed by clicking a tab on the screen. Representative categories include, but are not limited to, financial planning, calculators, government sites, medical information and product sites, online support groups, and state benefit programs. The web resources are updated regularly. The resources viewed by any given Visitor may vary depending upon the information provided during Registration.

This category of Visitor also has access to the MyCalendar 54 feature. MyCalendar is a computer program hosted by the Service Provider available via a link and can be used to schedule appointments, meetings and tasks. The Visitor can set reminders and print the calendar entries as desired.

Also, the Log In 20 provides access to the web-based community by a Visitor who is a customer of the Service Provider with an active account 56. By way of example, a Visitor may be a customer of the Service Provider if the Service Provider is providing one of its proprietary services, such as representation before the SSA to obtain SSDI or other SSA benefits, or providing the Visitor/customer with MAS, DLPS or similar service. Once a Visitor is a customer of the Service Provider, that Visitor will engage in Account Activation 50. Account Activation is required of all customers regardless of the service. Moreover, the customer is required to engage in Account Activation only one time even if the customer is receiving more than one proprietary service. It will be appreciated from FIG. 2 that this category of Visitor has access to all the features of the web-based community of the present invention as the previously described categories as well as three significant features, MyClaim 14, MyAMA Account 16 and MyLifePlan 18. These features will be explained in greater detail hereinafter and in reference to FIGS. 3 and 4.

Figure 3:
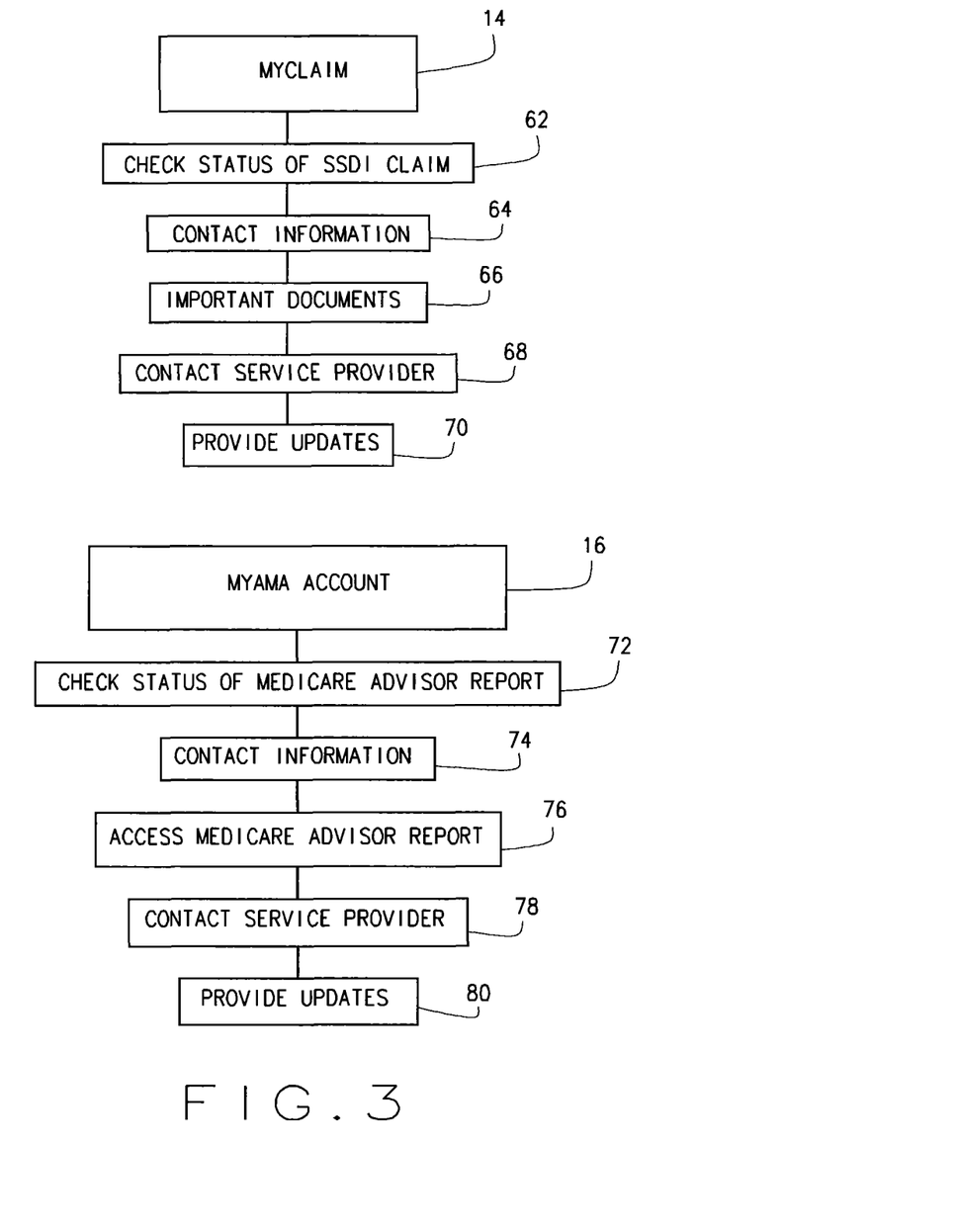
FIG. 3 is a block diagram illustrating aspects of a MyClaims and MyAMA Account component of the present invention.

For a Visitor/customer who has hired the Service Provider to help obtain SSDI, the Visitor/customer can activate his or her SSDI account through Account Activation 50. Upon receipt of a Form SSA-1696 (Appointment of Representative), the Service Provider sends the Visitor/customer an email containing an Activation ID and an Activation Key, required for activation and to maintain confidentiality and security. Account Activation, in general, allows the Visitor/customer to obtain details regarding the Visitor/customer's SSDI claim being handled by the Service Provider through the MyClaim 14 feature. Hence, MyClaim 14 is available to Visitors who are customers of the Service Provider's SSDI representation service. MyClaim 14 allows the Visitor/customer to check the status of his or her SSDI claim 62. The data regarding the Visitor/customer's claim is maintained in an appropriate and secure database.

The site provides a graphic that illustrates the status of the Visitor/customer's SSDI claim and the current level of the claim within the SSDI process. The Visitor/customer can check the status of his or her claim, the history of the Visitor's SSDI claim(s), information on the progress of the claim(s), and information regarding what the Visitor should expect by way of disposition of the claim in the future. The graphic reflects the progression of the claim through the SSDI process. The Visitor/customer is provided links to various levels of claims activity so as to determine the relative level of his or her claim. The Visitor/customer also can update his or her contact information 64 maintained in the database. The Visitor/customer also can change or update his or her personal information. The Visitor/customer also can inform the Service Provider if his or her banking information changes.

The Visitor/customer also can access a database containing his or her important documents 66 online through a secure website. These documents can include, but are not limited to, financial agreements and legal documents which can be filled out online or printed and filled out. Copies of completed forms can be printed and saved. Representative examples include, but are not limited to the Visitor/customer's completed Form SSA-1696 Form (Appointment of Representative) and fee agreement. The Visitor/customer also can view and download blank Form SSA-1696, SSA-795 (Direct Deposit Form), and Authorization for Release of Medical Information.

The Visitor/customer also can contact the Service Provider 68 through a customized Contact form that provides for an auto-populated feature containing the Visitor/customer's personal identification information. The Visitor/customer also can contact the Service Provider by telephone. In any event, the Visitor/customer can submit a question to the Service Provider about the SSDI claims process and the status of his or her claim. Furthermore, the Visitor/customer can provide relevant updates 70 to the Service Provider. The updates may include, but are not limited to, information sent directly to the Visitor/customer by the Department of Developmental Services (DDS) or SSA, any life changing events the Visitor/customer may recently have experienced, or an update on the Visitor/customer's medical condition(s).

For a Visitor who is a customer of the Service Provider's MAS, upon payment of the fee for service, the Service Provider sends the Visitor/customer an email including an Activation ID and Activation Key (required for activation) that allows the Visitor/customer to access MyAMA Account 16. Hence, this aspect of the invention is available to those customers of the Service Provider that have purchased the Service Provider's MAS. Allsup Medicare Advisor® is one representative example of a MAS provided by the assignee Service Provider. It is designed to aid disabled individuals or participants who may qualify for Medicare, for example a non-disabled individual age sixty-five (65) or older, to select a proper Medicare program, such as a Medicare Advantage Plan or a traditional Medicare plan that meets specific needs or criteria of the Visitor/customer and assists them with the enrollment process.

MAS provides a customized Medicare Advisor report tailored to the Visitor/customer's needs based upon data provided by the Visitor/customer. The data received is put into the Service Provider's systems, for example, into a computer system. The data is appropriately analyzed and compared to a database of available Medicare plans. The Visitor/customer can check the status of the Medicare Advisor report 72. MyAMA Account 16 is a secure link that allows the Visitor to check the status of his or her Medicare Advisor report 72 and complete the MAS questionnaire, which is required to create the Medicare Advisor report. The status check informs the Visitor/customer of any tasks that need to be completed in order to receive a complete report. The Visitor can review and update his or her contact information 74.

The completed Medicare Advisor report outlines all the Medicare options available, highlighting the top three that most closely match the Visitor/customer's criteria based upon a comparison the Visitor/customer's information with the database of Medicare plans. The Visitor/customer can access the completed Medicare Advisor report 76 through the MyAMA Account 16 aspect of the present invention to review the report and recommendations. The report is provided in a PDF format. This aspect of the invention also provides a tutorial on how to read the report. All purchased reports are available here for viewing, download or saving.

MyAMA Account 16 allows the Visitor to contact the Service Provider 78 through a custom contact form that automatically fills with the Visitor's information. The Visitor can contact the Service Provider by telephone. The Visitor also can contact the Service Provider 24 hours a day, which provides a supportive, accessible community of resources and information around the clock. The Visitor also can provide updates 80 to update contact information in the database or even refer a friend to the service. Individuals using the MAS aspect of the invention have access to the program specialists, either through the MyAMA Account 16 or by telephone to receive timely responses to questions. MAS is described in greater detail in assignee's U.S. patent application Ser. No. 12/704,120, which is incorporated herein by reference.

Figure 4:
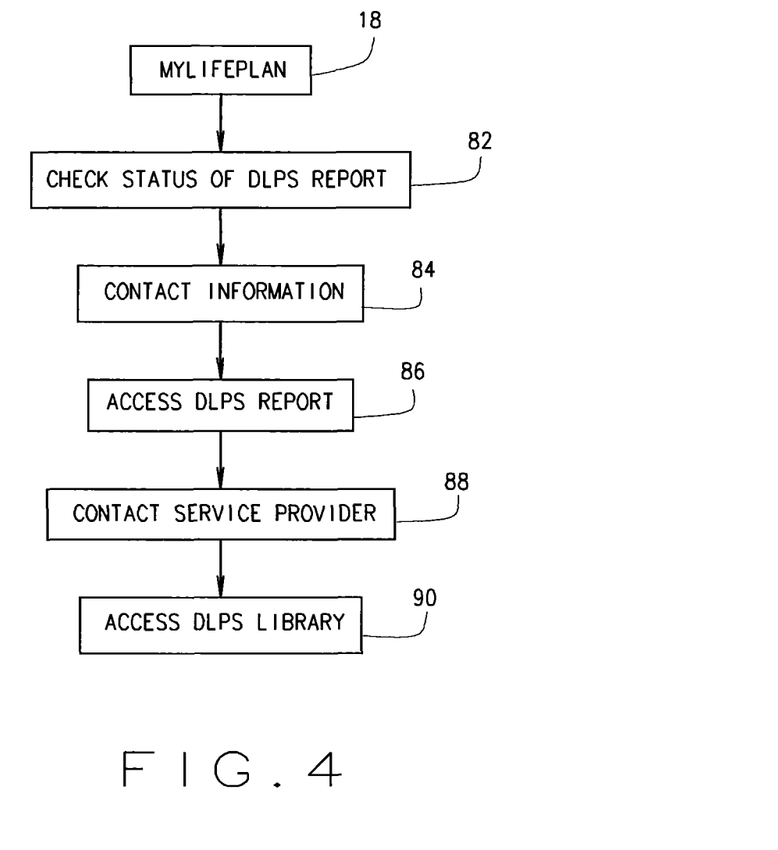
FIG. 4 is a block diagram illustrating aspects of MyLifePlan.

A Visitor/customer who is a customer of the Service Provider's Disability Life Planning Service® (DLPS) with an activated account can access various aspects of MyLifePlan 18 after logging on as well. Aspects of MyLifePlan 18 are illustrated in FIG. 4. As mentioned above, DLPS comprises methods and a system for providing an array of optimized services to a disabled individual including, but not limited to, obtaining SSDI benefits from the SSA, management of lump sum payments of retroactive SSDI, comprehensive lifestyle and financial planning for individuals with disabilities, Medicare Advisor Service, tax planning, healthcare discount services and financial management through the use of stored value cards and accounts.

For a Visitor who is a customer of the Service Provider's DLPS, upon payment or promise of payment of the fee for service, the Service Provider sends the Visitor/customer an email including an Activation ID and Activation Key (required for activation) that allows the Visitor/customer to access MyLifePlan 18. Hence, this aspect of the invention is available to those customers of the Service Provider that have purchased the Service Provider's DLPS.

DLPS provides a customized report tailored to the Visitor/customer's needs based upon data provided by the Visitor/customer. The data received is put into the Service Provider's systems, for example, into a computer system. The data is appropriately analyzed and compared to a database of available financial and other related helpful resources. The Visitor/customer can check the status of the DLPS report 82. MyLifePlan 18 is a secure link that allows the Visitor to check the status of his or her DLPS report 82 and complete the DLPS questionnaire, which is required to create the DLPS report. The status check informs the Visitor/customer of any tasks that need to be completed in order to receive a complete report. The Visitor can review and update his or her contact information 84.

The completed DLPS report outlines many financial and other helpful resources available, taking into consideration the customer's specific needs and situation as specified in the questionnaire. The Visitor/customer can access the completed DLPS report 86 through the MyLifePlan 18 aspect of the present invention to review the report and recommendations. The DLPS report 86 is provided in a PDF format. This aspect of the invention also provides a tutorial on how to read the report.

MyLifePlan 18 allows the Visitor to contact the Service Provider 88 through a custom contact form that automatically fills with the Visitor's information. The Visitor can contact the Service Provider by telephone. The Visitor also can contact the Service Provider 24 hours a day, which provides a supportive, accessible community of resources and information around the clock. The Visitor also can access the DLPS Library 90, which is a collection of additional resources and information in addition to what is contained within the DLPS report. Individuals using the DLPS have access to the program specialists, either through the MyLifePlan 18 or by telephone to receive timely responses to questions. DLPS also is described in greater detail in assignee's U.S. patent application Ser. No. 12/704,120, which is incorporated herein by reference.

It will be appreciated that the foregoing description is illustrative of the broad aspects of the invention and represents the best mode of carrying out the invention presently known by the inventors. Any modifications or changes in the web-based community are intended to be included within the scope of the invention. Furthermore, various modifications and changes can be made in the foregoing detailed description without departing from the scope of the invention. Therefore, the description and accompanying drawings are intended to be illustrative only and should not be construed in a limiting sense.

The invention claimed is:

1. A method of providing access to an interactive web-based community to obtain personalized information and resources consisting essentially of information and resources relevant to an individual with a mental or physical disability provided through the web-based community, comprising:
   allowing access by a visitor, through an appropriately programmed computer, to a website hosted by a Service Provider, the website comprising at least one link to a single portal;
   allowing access by the visitor to said portal through the link;
   allowing access by the visitor through the portal to one or more databases containing data consisting essentially of a plurality of resources and services relevant to an individual with a mental or a physical disability; and
   providing to the visitor, through single portal, personalized information about resources and services relevant to an individual with a mental or a physical disability from one or more of the databases, said personalized information related to one or more of information relevant to an individual with a mental or physical disability, to a claim for Social Security Disability Insurance (SSDI), to a comprehensive life plan, or to a Medicare advisor service;
   wherein at least one of the databases has stored personal data about the individual's mental or a physical disability and the individual's locale, and the information obtained is personalized to said individual based upon said stored personal data.

2. The method of claim 1 wherein at least one of the databases has stored data on a claim for SSDI filed on behalf of an individual with a mental or physical disability and the information obtained is a report on the status of said individual's claim for SSDI.

3. The method of claim 2 wherein at least one of the databases comprises information required to file a claim for SSDI submitted to the Service Provider by the individual.

4. The method of claim 1 wherein at least one of the databases has stored personal data about an individual's mental or physical disability and the individual's locale and at least one of the databases has stored data regarding a plurality of Medicare plans and the information obtained is Medicare plan information personalized to said individual based upon a comparison of the stored personal data regarding the individual's mental or physical disability and the individual's locale and the stored Medicare plans data.

5. The method of claim 4 wherein the information and resources obtained is a report comprising at least three Medicare plans.

6. The method of claim 1 wherein the comprehensive life plan comprises disability life planning services for the individual with a mental or a physical disability.

7. The method of claim 6 wherein the disability life planning services comprise one or more services selected from the group of services consisting of obtaining SSDI benefits from the Social Security Administration (SSA); management of lump sum payments of retroactive SSDI; comprehensive lifestyle and financial planning for individuals with disabilities; Medicare Advisor Service; tax planning; healthcare discount services; and financial management.

8. The method of claim 1 wherein at least one of the databases comprises news of interest to an individual with a physical or mental disability.

9. The method of claim 1 wherein at least one of the databases comprises an on-line forum of interest to an individual with a physical or mental disability.

10. The method of claim 1 wherein at least one of the databases has stored personal data about an individual with a mental or physical disability and at least one of the databases comprises data regarding at least one of a.) obtaining SSDI benefits from the Social Security Administration (SSA), b.) management of lump sum payments of retroactive SSDI benefits, c.) comprehensive lifestyle planning for individuals with disabilities, d.) financial planning for individuals with disabilities, e.) Medicare plans, f.) tax planning, g.) healthcare discount services or h.) financial management; and
   the information obtained is at least one of a.) information or resources regarding filing and monitoring a claim for SSDI benefits from the SSA, b.) management of lump sum payments of retroactive SSDI benefits, c.) comprehensive lifestyle planning for individuals with disabilities, d.) financial planning for individuals with disabilities, e.) Medicare plans, f.) tax planning, g.) healthcare discount services or h.) financial management, said information personalized to said individual based upon the stored personal data.

11. The method of claim 1 wherein the healthcare discount services and financial management are facilitated through the use of stored value cards and accounts.

12. The method of claim 1 further comprising a step of allowing an individual to interact with other visitors.

13. The method of claim 1 wherein the individual and the visitor are the same person.

14. A method for accessing an interactive website and obtaining information relevant to an individual with a mental or physical disability, comprising:
   permitting access by a visitor, through a computer specifically programmed to carry out steps of the method, to a website hosted by a Service Provider,
   permitting access by the visitor through a single website portal to at least one database storing data consisting of data associated with at least one of a claim for Social Security Disability Insurance (SSDI) filed on behalf of the visitor, personalized comprehensive disability life plans, or a Medicare advisor program; and
   permitting the visitor to obtain through the computer information about one or more of a status of the claim for SSDI, a personalized comprehensive disability life plan, or personalized Medicare advice.

15. The method of claim 14 further comprising the step of permitting access by the visitor to at least one database comprising stored personal data about the visitor including the visitor's locale, and at least one database that has stored data regarding a plurality of Medicare plans and permitting the visitor to obtain, through the computer, Medicare plan information personalized to the visitor based upon a comparison of the stored personal data and the stored Medicare plans data.

16. The method of claim 14 further comprising the step of permitting access by the visitor to at least one database consisting essentially of stored data regarding an array of services for a disabled individual, said array of services comprising at least one of i.) data regarding obtaining SSDI benefits from the Social Security Administration (SSA), ii.) management of lump sum payments of retroactive SSDI, iii.) comprehensive lifestyle and financial planning for an individual with a disability, iv.) a Medicare Advisor Service, v.) tax planning, vi.) healthcare discount services, or vii.) financial management.

17. A method for accessing an interactive website and obtaining information relevant to an individual with a mental or physical disability, comprising:

permitting access by a visitor, through an appropriately programmed computer, to a website hosted by a Service Provider;

permitting access by the visitor through a single website portal to at least one database storing data consisting essentially of data associated with a personalized record of a claim for Social Security Disability Insurance (SSDI) filed on behalf of the visitor;

permitting the visitor to obtain through the computer information about the status of the claim for SSDI filed on behalf of the visitor;

permitting access by the visitor through said single website portal to at least one database comprising stored personal data about the visitor including the visitor's locale, and at least one database that has stored data consisting essentially of a plurality of Medicare plans and permitting the visitor to obtain, through the computer, information regarding one or more Medicare plans personalized to the visitor based upon a comparison of the stored personal data and the stored Medicare plans data;

permitting access by the visitor through said single website portal to at least one database comprising stored data regarding an array of services for a disabled individual said array of services comprising at least one of data regarding obtaining SSDI benefits from the Social Security Administration (SSA), management of lump sum payments of retroactive SSDI, comprehensive lifestyle and financial planning for an individual with a disability, a Medicare Advisor Service, tax planning, healthcare discount services or financial management; and permitting the visitor to interact with other visitors to the website.

* * * * *